United States Patent [19]

Wells

[11] 4,074,964
[45] Feb. 21, 1978

[54] METHOD OF COLORING HAIR USING A PRESSURE SENSITIVE ADHESIVE

[76] Inventors: H. David Wells, 201 178th Drive, North Miami Beach, Fla. 33160

[21] Appl. No.: 720,553

[22] Filed: Sept. 7, 1976

[51] Int. Cl.$^2$ .......................... A61K 7/13; G02B 27/00
[52] U.S. Cl. .......................................... 8/10.2; 8/10.1; 132/7; 350/172; 350/236
[58] Field of Search .................... 8/10.1, 10.2, 10, 11, 8/32; 132/7; 350/33, 91, 172, 17, 236; 250/330, 333

[56] References Cited

U.S. PATENT DOCUMENTS

| | | | |
|---|---|---|---|
| 3,349,781 | 10/1967 | Poole et al. | 132/7 |
| 3,433,232 | 3/1969 | Garrett | 132/7 |
| 3,464,424 | 9/1969 | Buzzelli | 132/7 |

Primary Examiner—Albert T. Meyers
Assistant Examiner—Vera C. Clarke

[57] ABSTRACT

A method of coloring hair which consists of parting the hair in a manner so as to define a plurality of individual hair sectors on the subject's scalp, all of the hair in each sector extending from the scalp outwardly in generally the same direction toward a peripheral edge. A commercially available hairdresser's tape is applied to the subject's scalp along all of the part lines and a double-side adhesive tape is applied over the hairdresser's tape. One or more discrete hair tress segments are wrapped in generally rectangular pieces of a suitable liquid impervious sheet material along with a hair coloring solution. Each of the packets of hair so formed is placed in a spanning relation to two adjacent pieces of the double-side adhesive tape and the opposed end portions thereof are put in contact with the outer, exposed adhesive side of the two pieces of tape. The packets are adhesively held in this position during the hair treatment time after which they are removed, unrolled and the tape is stripped from the subject's head.

4 Claims, 4 Drawing Figures

METHOD OF COLORING HAIR USING A PRESSURE SENSITIVE ADHESIVE

FIELD OF THE INVENTION

The present invention pertains to a method of coloring hair, particularly for defining a predetermined pattern of colored streaks therein.

BACKGROUND OF THE PRESENT INVENTION

One of the most widely used methods of color streaking hair comprises the use of a perforated cap which is placed over the head of the subject. Hook means such as a crocheting hook is pushed through the perforations to selectively engage locks of hair which are pulled through the perforations to overlie the outer surface of the cap to receive a color treatment.

Another currently used method comprises the rolling of selected locks of hair in pieces of sheet material along with a coloring solution and then clipping the packets of hair in place to the adjacent hair. The number of clips used is limited by space. In addition, this method is time-consuming, causes pain to the subject because of pulling, greatly limits the patterns and, because clips often don't hold securely, slippage creates a problem.

Therefore, one of the principal objects of the present invention is to provide a method of color streaking hair which greatly reduces the discomfort to the subject, substantially reduces the operating time, provides for unlimited patterns and enables the operator to process a single lock of hair with more than one color.

Another principal object of this invention is to provide a method of color streaking hair which utilizes a pressure sensitive tape means, fixed to the scalp, to securely hold packets of hair and a coloring solution in place while exposing virtually all of the subject's hair, permitting an unlimited selection of color patterns.

A further object of the invention is to provide a method of color streaking hair which utilizes very inexpensive, commercially available disposable products which may be rapidly applied to the subject and removed after the coloring operation with no discomfort to the subject.

DETAILED DESCRIPTION OF THE METHOD OF THE PRESENT INVENTION

Figure 1:
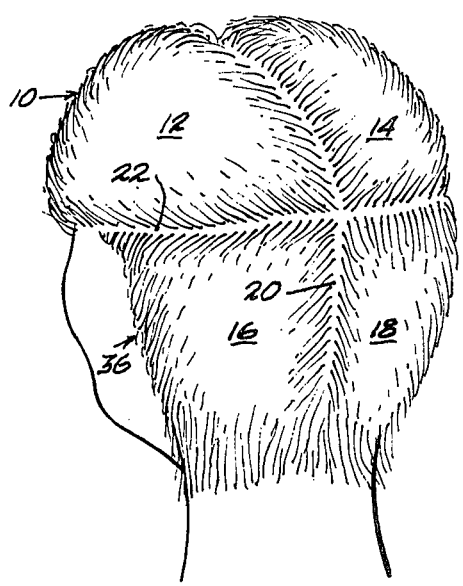
FIG. 1 is a rear perspective view of a head with the hair parted in a manner so as to define a plurality of individual hair sectors in accordance with the first step of the method.

With reference to the drawings in which like reference characters designate like or corresponding parts throughout the various views, and with particular reference to FIG. 1, the hair 10 of the subject's scalp is divided into four sectors 12, 14, 16 and 18 by part lines 20 and 22 for purposes of illustration. In practice, the number and pattern of the sectors may vary.

Figure 2:
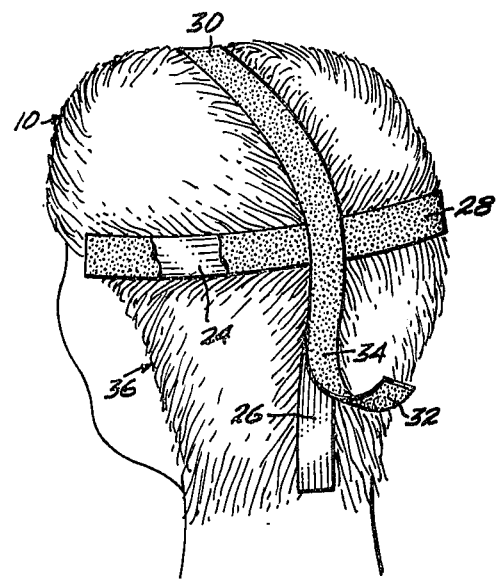
FIG. 2 is view similar to FIG. 1 illustrating second and third steps of the method.

With reference to FIG. 2, two lengths of hairdresser's tape 24 and 26 are fixed along the part lines 20 and 22 and similar lengths of double-side adhesive tape 28 and 30 are fixed to the lengths of hairdresser's tape 24 and 26 in a covering relation thereto. The inner and outer surfaces of tape lengths 28 and 30 are provided with a pressure sensitive adhesive as at 32 and 34.

As illustrated in the drawings, all of the hair in each sector 12, 14, 16 and 18 is combed outwardly in generally the same direction toward an outer peripheral edge, generally indicated at 36.

Figure 4:
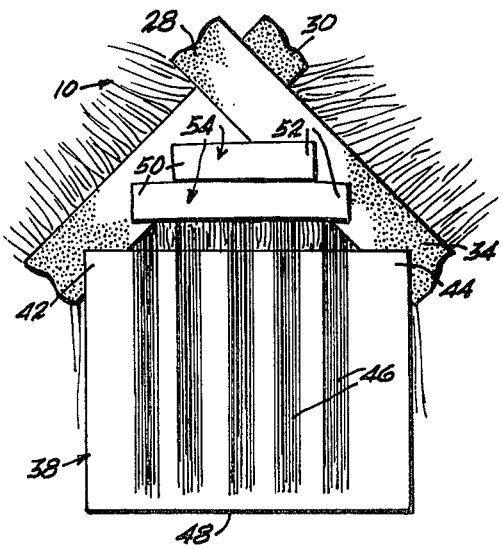
FIG. 4 is an enlarged elevational view of a portion of the subject's scalp illustrating a plurality of discrete locks of hair positioned on a generally rectangular sheet formed of a suitable liquid impervious material.

Referring now to FIG. 4, the color streaking operation is sequentially performed in the sectors 12, 14, 16 and 18 in the following manner. A generally rectangular sheet 28 of a suitable liquid impervious material is placed against the outer surface of the hair and one or more discrete locks of hair is lifted to an overlying relation to the top surface of the sheet 38. It should be noted that the corners 42 and 44 of sheet 38 contact the outer surface adhesive 34 of tape lengths 28 and 30 to maintain said sheet 38 in place. After the lock or locks of hair 46 are disposed as in FIG. 4, the coloring solution is applied thereto and the sheet 38 is rolled up from the bottom edge 48 and the opposed end portions 50 and 52 are pressed against the outer surface adhesive 34 of tape lengths 28 and 30 to maintain the hair packets such as 54 in place. Sheets 38 are preferably formed of a suitable plastic material such as the commercially available product sold under the trade name "Saran Wrap".

Figure 3:
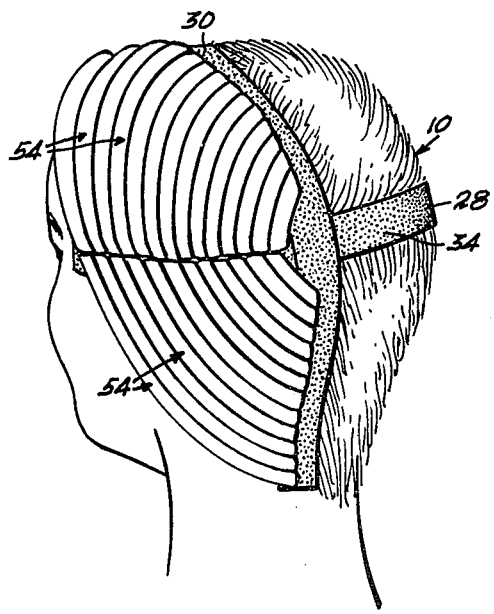
FIG. 3 is a view similar to FIG. 2 illustrating a further step of the method.

FIG. 3 illustrates hair packets 54 in a converging relation to one-half of the subject's scalp. However, it should be understood that the number of locks of hair 46 in each packet and the number of packets 54 is determined by the desired streaking pattern. After a predetermined period of drying time, the packets 54 are unrolled, and the tape lengths 24, 26 and 28, 30 are stripped from the subject's head.

What is claimed is:

1. A method of coloring hair comprising, separating the hair of a subject's scalp to define a plurality of individual sectors, separated by part lines; applying tape means along the length of each of said part lines, said tape means providing a pressure-sensitive adhesive on the inner surface thereof contacting said part lines and on its outer surface; separating at least one discrete lock of hair from the area within one of said sectors and laying the same on a thin, flexible, liquid impervious sheet sized to lengthwisely span and to overlie at least a portion of the outer surface of at least two adjacent lengths of said tape means; applying a coloring solution to said discrete lock of hair and rolling said lock in said sheet toward the root ends thereof to form a pocket of hair and coloring solution, and pressing opposed end portions of said packet into engagement with said outer surface pressure-sensitive adhesive of said two adjacent lengths of tape means for securing purposes.

2. The method as defined in claim 1 wherein aid procedure for forming and securing a packet of hair and coloring solution is repeated, relative to each of said sectors, a predetermined number of times to form a desired pattern of color streaking.

3. The method as defined in claim 1 wherein said tape means comprises a first tape layer of hairdresser's tape having a single surface provided with a pressure-sensitive adhesive, secured along the length of each of said part lines, and a second tape layer of a type providing a pressure-sensitive adhesive on both surfaces secured in an overlying relation to said first tape layer.

4. The method as defined in claim 2 wherein said packets are subjected to a drying procedure, whereupon each of said packets is removed, unrolled, and the tape is stripped off the subject's head.

* * * * *